United States Patent [19]

Gammill

[11] Patent Number: 4,490,547

[45] Date of Patent: Dec. 25, 1984

[54] ANTIATHEROSCLEROTIC BENZOPYRANS

[75] Inventor: Ronald B. Gammill, Portage, Mich.

[73] Assignee: The Upjohn Company, Kalamazoo, Mich.

[21] Appl. No.: 546,004

[22] Filed: Oct. 27, 1983

Related U.S. Application Data

[62] Division of Ser. No. 378,700, May 17, 1982, Pat. No. 4,438,274.

[51] Int. Cl.³ .......................................... C07D 311/78
[52] U.S. Cl. ...................................................... 549/387
[58] Field of Search .......................................... 549/387

[56] References Cited

U.S. PATENT DOCUMENTS 2,680,119 6/1954 Robertson et al. ................. 549/387
4,284,569 8/1981 Gammill ............................. 549/387

OTHER PUBLICATIONS

Abu-Shady, H., Experiments with Khellin VII., UAR J. Pharm. Sci., 11:283-288 (1970).
Abu-Shady, H. et al., Experiments with Khellin-VIII, J. Pharm. Belg. 33:397-399 (1978).
Anrep, G. V. et al., Therapeutic Uses of Khellin, The Lancet, pp. 557-558 Apr. 26, 1947.
Anrep, G. V. et al., The Coronary Vasodilator Action of Khellin, Amer. Heart J., 37:531-542 (1949).
Apffel, C. A., Die Zytostatische Wirkung von Chinonen und Ihren Derivaten, Deut. Med. Wochschr., 80:414-416 (1955).
Aubertin, E., La Khelline, Agent de Relachement de la Musculature Lisse, J. Med. Bordeaux, 127:821-823 (1950).
Baytop, O. T., Khellin'in Yer Solucanlarina Tesiri Hakkinda, Folia Pharm. (Turkey), 1:48-49 (1949).
Best, M. M., et al., Effects of Dioxyline Phosphate and Enteric-Coated Khellin on Coronary Artery Insufficiency, Amer. J. Med. Sci. 222:35-39 (1951).
Chen, G. et al., The Central Nervous Depressive Effect of Khellin, Proc. Soc. Expetl. Biol. Med., 78:305-307 (1951).
Colombo, G., et al., Sulla Attivita di alcune Sostanze del Gruppo Della Kellina Sulla Motilita Ureterale—in vitro—, Arch. Sci. Med. 97:71-81 (1954).
Day, C. E., et al., Utility of a Selected Line (SEA) of the Japanese Quail for the Discovery of New Anti-Atherosclerosis Drugs, Laboratory Animal Science, 27:817-821 (1977).
Eaton, R. P., High Density Lipoprotein-Key to Anti--Atherogenesis, J. Chron. Dis., 31:131-135 (1978).
Haust, M. D., Reaction Patterns of Intimal Mesenchyme to Injury, and Repair in Atherosclerosis, Adv. Exp. Med. Biol., 43:35-57 (1974).
Huttrer, C. P. et al., The Chemistry and Physiological Action of Khellin and Related Products, Chem. Revs., 48:543-579 (1951).
Jordan, H., Cardiovasculare Wirkungen Intravenoser Khellin-Injektionen, Arzneimittel-Forsch, 7:82-85 (1957).
LaBarre, J., et al., A Propos de l'Action Inhibitrice de la Khelline dans l'Ulcere Gastrique Experimental Provoque par Administration Journaliare de Phenylbutazone, Compt. Rend. Soc. Biol., 150:1806-1807 (1956).
Montorsi, W., et al., Sur l'Activite de Certaines Substances du Groupe de la Khelline, Presse Med., 63:81 (1955).
Musante, C., et al., Furil E. Isossazol-Furo-Cromoni e Derivati, Pharmaco. (Pavie) Ed. Sci., 15:81-94 (1960).
Mustafa, A., et al., Experiments with Furochromones, Synthesis of Ammiol and Khellol, J. Org. Chem., 26:886-890 (1961).
Mustafa, A., Furopyrans and Furopyrones, John Wiley and Sons, Inc., NY (1967) pp. 102-159 (Chapter III: Furochromones).
Osher, H. L. et al., Khellin in the Treatment of Angina Pectoris, New England J. Med., 244:315-321 (1951).
Raymond-Hamet, M., Compt. Rend., 238:1624-1626 (1954).
Samaan, K. et al., The Response of the Heart to Visammin and to Khellinin, J. Pharm. Pharmacol., 1:538-544 (1949).
Samaan, K. et al., The Existence in Ammi Visnaga of a Cardiac Depressant Principle Visammin and a Cardiac Stimulant Glycoside Khellinin, J. Roy, Egypt Med. Assoc., 33:953-960 (1950).
Schonberg, A., et al., Khellin and Allied Compounds, JACS 72:1611-1617 (1950).
Schonberg, et al., Furo-Chromones and -Coumarins. XIV. JACS 77:5439-5440 (1955).
Schurr, P. E., High Volume Screening Procedure for Hypobetalidoproteinemia Activity in Rats, Adv. Exp. Med. Biol. 67: Atherosclerotic Drug Discovery, pp. 215-229, Plenum Press (1975).
Silber, E. N., The Effect of Khellin on Cardio-Pulmonary Function in Chronic Pulmonary Disease, published in 1951, pp. 1046-1054.
Swayne, V. R. et al., Spermicidal Action of Khellin, Amer. J. Pharm., 125:295-298 (1953).

*Primary Examiner*—Nicky Chan
*Attorney, Agent, or Firm*—Lawrence T. Welch

[57] ABSTRACT

The present invention provides certain novel benzopyrans which are useful for antiatherosclerotic purposes.

2 Claims, No Drawings

ANTIATHEROSCLEROTIC BENZOPYRANS

CROSS REFERENCE TO RELATED APPLICATIONS

This application is a divisional of co-pending application 378,700, filed May 17, 1982, now U.S. Pat. No. 4,438,274.

BACKGROUND OF THE INVENTION

The present invention provides novel anti-atherosclerotic benzofurans, the use and preparation of which are described in U.S. Pat. No. 4,438,274 which is incorporated herein by reference.

PRIOR ART

Extensive pharmacological uses for khellin and related substances are known, as indicated in U.S. Pat. No. 4,438,274. Khellin analogs are also known in the art. See, e.g., U.S. Pat. No. 4,284,569 and the review by Mustafa, "Furopyrans and Furopyrones," John Wiley and Sons, Inc., N.Y., N.Y. (1976) pages 102–159 and U.S. Pat. No. 2,680,119 which describes 6 and/or 7-substituted furochromones, i.e., alkyl, alkoxyalkyl, and phenylalkyl substituted compounds.

SUMMARY OF THE INVENTION

The present invention provides:
a benzopyran of formula III
wherein $R_{14}$ is
(1) hydrogen;
(2) alkyl of one to 8 carbon atoms, inclusive;
(3) alkoxymethyl of 2 to 8 carbon atoms, inclusive;
(4) alkylthioalkyl of 2 to 8 carbon atoms, inclusive;
(5) trifluoromethyl;
(6) phenoxymethyl;
(7) phenylthiomethyl;
(8) phenoxymethyl or phenylthiomethyl substituted by chloro, fluoro, trifluoromethyl, alkyl of one to 3 carbon atoms or alkoxy of one to 8 carbon atoms; or
(9) cycloalkyl of 3 to 10 carbon atoms, inclusive; and wherein one of $R_5$ and $R_6$ is methoxy and the other is hydrogen or $R_5$ and $R_6$ are both methoxy.

DESCRIPTION OF THE PREFERRED EMBODIMENTS

The present invention particularly provides 4,9-dimethoxy-7-methyl-7H-furo[3,2g][1]benzopyran.

I claim:

1. A benzopyran of formula III

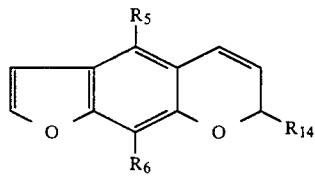

wherein
$R_{14}$ is
(1) hydrogen;
(2) alkyl of one to 8 carbon atoms, inclusive;
(3) alkoxymethyl of 2 to 8 carbon atoms, inclusive;
(4) alkylthioalkyl of 2 to 8 carbon atoms, inclusive;
(5) trifluoromethyl;
(6) phenoxymethyl;
(7) phenylthiomethyl;
(8) phenoxymethyl or phenylthiomethyl substituted by chloro, fluoro, trifluoromethyl, alkyl of one to 3 carbon atoms or alkoxy of one to 8 carbon atoms; or
(9) cycloalkyl of 3 to 10 carbon atoms, inclusive; and wherein one of $R_5$ and $R_6$ is methoxy and the other is hydrogen or $R_5$ and $R_6$ are both methoxy.

2. 4,9-Dimethoxy-7-methyl-7H-furo[3,2-g][1]benzopyran, a compound according to claim 1.

* * * * *